US006932963B2

(12) United States Patent
Perricone

(10) Patent No.: US 6,932,963 B2
(45) Date of Patent: *Aug. 23, 2005

(54) TREATMENT OF SKIN WOUNDS USING POLYENYLPHOSPHATIDYLCHOLINE AND ALKANOLAMINES

(76) Inventor: Nicholas V. Perricone, 377 Research Pkwy., Meriden, CT (US) 06450

( * ) Notice: Subject to any disclaimer, the term of this patent is extended or adjusted under 35 U.S.C. 154(b) by 176 days.

This patent is subject to a terminal disclaimer.

(21) Appl. No.: 10/335,450

(22) Filed: Dec. 31, 2002

(65) Prior Publication Data

US 2003/0105063 A1 Jun. 5, 2003

Related U.S. Application Data

(63) Continuation-in-part of application No. 10/257,037, filed on Oct. 7, 2002, which is a continuation-in-part of application No. PCT/US00/17463, filed on Jun. 23, 2000, and a continuation-in-part of application No. PCT/US02/18026, filed on Aug. 22, 2002.

(51) Int. Cl.$^7$ ............ A61K 7/42; A61K 7/44; A61K 7/00; A61K 31/685; A61K 31/35; A61K 31/355

(52) U.S. Cl. ............ 424/59; 424/60; 424/400; 424/401; 514/78; 514/474; 514/456; 514/458; 514/847

(58) Field of Search ............ 424/59, 400, 401; 514/78, 474, 456, 458, 847

(56) References Cited

U.S. PATENT DOCUMENTS

| | | | |
|---|---|---|---|
| 4,235,793 A | 11/1980 | Betzing | |
| 4,963,527 A | 10/1990 | Bombardelli et al. | |
| 5,545,398 A | * 8/1996 | Perricone | 424/59 |
| 5,554,647 A | * 9/1996 | Perricone | 514/474 |
| 5,574,063 A | * 11/1996 | Perricone | 514/474 |
| 5,726,164 A | 3/1998 | Weder et al. | |
| 5,863,549 A | 1/1999 | Tarantino | |
| 5,885,486 A | 3/1999 | Westesen et al. | |
| 5,925,669 A | 7/1999 | Katz et al. | |
| 5,997,888 A | 12/1999 | Weder et al. | |
| 6,191,121 B1 | * 2/2001 | Perricone | 514/78 |
| 6,294,350 B1 | * 9/2001 | Peterson | 435/29 |
| 6,319,942 B1 | * 11/2001 | Perricone | 514/440 |

FOREIGN PATENT DOCUMENTS

| | | |
|---|---|---|
| EP | 86109256.7 | 7/1986 |
| EP | 88102321.2 | 2/1988 |
| EP | 88110861.7 | 7/1988 |
| WO | PCT/IB96/00493 | 5/1996 |

OTHER PUBLICATIONS

Aleynik, S.I., et al.; Journal Invest. Medicine 47: 507–512 (1999).
Ibbotson, S.H., et al.; Journal Invest. Dermatology 112: 933–938 (1999).
European Search Report, Dec. 17, 2003.

* cited by examiner

*Primary Examiner*—Shelley A. Dodson
(74) *Attorney, Agent, or Firm*—St. Onge Steward Johnston & Reens LLC

(57) ABSTRACT

Polyenylphosphatidylcholine in combination with an alkanolamine are topically applied to treat skin wounds, promote healing, and minmize scar formation. Typical compositions contain from about 0.25% to about 12% of a polyenylphosphatidylcholine preparation obtained from natural sources such as soybean oil which contains at least about 25% by weight, preferably about 40% or more, dilinoeoylphosphatidylcholine, and from about 0.1% to about 10% by weight of an alkanolamine such as ethylaminoethanol, methylaminoethanol, dimethylaminoethanol, isopropanolamine, triethanolamine, isopropanoldimethylamine, ethylethanolamine, 2-butanolamine, choline, serine, or mixtures thereof. Dimethylaminoethanol is a particularly preferred alkanolamine. Tyrosine is an adjunct ingredient in many embodiments.

30 Claims, No Drawings

TREATMENT OF SKIN WOUNDS USING POLYENYLPHOSPHATIDYLCHOLINE AND ALKANOLAMINES

RELATED APPLICATION DATA

This application is a continuation-in-part of U.S. application Ser. No. 10/257,037, filed 7 Oct. 2002, which was a continuation-in-part of PCT/US00/17463, filed internationally 23 Jun. 2000, which claimed priority benefit of U.S. application Ser. No. 09/543,947, filed 6 Apr. 2000, which issued as U.S. Pat. No. 6,191,121 on 20 Feb. 2001, and a continuation-in-part of PCT/US02/18026, filed internationally 22 Aug. 22, 2002, claiming priority benefit of U.S. application Ser. No. 09/875,317, filed 6 Jun. 2001, which issued as U.S. Pat. No. 6,319,942 on 20 Nov. 2001; U.S. application Ser. No. 09/900,680, filed 6 Jul. 2001; U.S. application Ser. No. 09/931,616, filed 16 Aug. 2001; and U.S. application Ser. No. 10/085,864, filed 27 Feb. 2002.

BACKGROUND OF THE INVENTION

1. Field of the Invention

This invention relates to the topical application of polyenylphosphatidyl choline and alkanolamines such as dimethylaminoethanol for the treatment of skin wounds. Therapies according to the invention are particularly efficacious for promoting healing of minor cuts, abrasions, burns, and surgical wounds, and for preventing scar formation.

2. Description of Related Art

Skin inflammation, wound healing, and aging are closely related phenomena. In acute inflammation, there is typically a respiratory burst of neutrophil activity that initiates cascades involving a change in the oxidation state of the cell. Acute inflammation is also characterized by mast cell degranulation wherein serotonin is produced, which acts as a signal transduction factor. Following that, excited oxygen species are generated, e.g., superoxide anion, and these damage the lipid-rich membranes and activate the chemical mediators of the proinflammation and inflammation cascades.

Alteration in the redox state of the cell activates transcription factors such as NFκB as well as AP1, which then causes production of proinflammation mediators. These mediators, also known as cytokines, e.g., TNFα and various interleukins, result in inflammation. Arachadonic acid is released, which is oxidized to biologically active mediators. When arachadonic acid is oxidized via the cyclooxygenase or lipoxygenase pathways, for example, prostaglandins, leukotrines, and hyroxyeicosatetraenoic acid (HETE) are produced, which cause erythma, edema, and free radical production. Transcription factors such as NFκB and AP1 alter DNA expression in the cell and produce cytokines and proteinases such as collagenase.

Similar metabolic events are observed in skin aging. Cell age is due in part to free radical damage, which takes place mostly within the cell membrane. The cell membrane is most susceptible to attack by free radicals because of its dense molecular structure largely comprising lipids and lipoproteins, which are easily oxidized by reactive oxygen species. In skin, reactive oxygen species such as singlet oxygen, the superoxide anion, and hydroxyl radicals, as well as other free radicals, are generated in normal metabolism, as well as through ultraviolet sun exposure, other forms of radiation, other environmental factors such as pollution or exposure to chemicals in the home or workplace, and the like, active in the arachidonic acid cascade. As in inflammation, free radicals activate chemical mediators that produce prostaglandins and/or leukotrines.

The body contains an endogenous antioxidant defense system made up of antioxidants such as vitamins C and E, glutathione, and enzymes, e.g., superoxide dismutase. When metabolism increases or the body is subjected to other stress such as infection, extreme exercise, radiation (ionizing and non-ionizing), or chemicals, the endogenous antioxidant systems are overwhelmed, and free radical damage takes place. Over the years, the cell membrane continually receives damage from reactive oxygen species and other free radicals, resulting in cross-linkage or cleavage or proteins and lipoprotins, and oxidation of membrane lipids and lipoproteins. Damage to the cell membrane can result in myriad changes including loss of cell permeability, increased intercellular ionic concentration, and decreased cellular capacity to excrete or detoxify waste products. As the intercellular ionic concentration of potassium increases, colloid density increases and m-RNA and protein synthesis are hampered, resulting in decreased cellular repair. Some cells become so dehydrated they cannot function at all.

Scars result from wound healing, which occurs in three separate phases: inflammation, formation of granulation tissue, and matrix formation. (For a review, see Sahl, W. J., and Clever, H., *Internat. J. Derm.*, 1994, 33: 681–691 (part I) and 763–769 (part II); this paper, and others and patents cited below are expressly incorporated herein in their entireties by reference). During the first phase, damage to endothelial cells, complement, and platelets at the wound site release chemotactic factors that result in the infusion of neutrophils, lymphocytes and macrophages, which aids in the removal of infection and foreign debris. As in all inflammatory processes, there is generation of free radicals, which damages cell membranes and results in formation of oxidized proteins and fats, and cross-linked new collagen, laying a scaffold for the next phase.

At the end of the inflammatory phase, the granulation phase begins with an influx of fibroblasts and endothelial cells to the wound. Other key cells in this phase are macrophages and platelets. Macrophages induce the beginning of granulation by relasing platelet-derived growth factor (PDGF), tumor necrosis growth factor (TGF)-α, and an epidermal growth factor-like substance. Activated platelets release epidermal growth factor (EGF), PDGF, TGF-α, and TGF-β. Together these play roles in the re-epithelialization process wherein keratinocytes cells migrate in sheaths over a provisional matrix consisting primarily of fibrin, fibronectin, type V collagen, and tenascin, and produce their own fibronectin receptors.

Once re-epithelilization has occurred, keratinocytes resume their normal differentiated form, and matrix formation begins. Matrix formation consists primarily of the construction of dermal matrix, which is regulated by fibroblasts. Chemotaxis of fibroblasts results in the production of abundant quantities of hyaluronate, fibronectin, and types I and III collagen. These components comprise the bulk of the provisional extracellular matrix in the early part of this wound repair phase. Hyaluronic acid (HA) creates an open-weave pattern in the collagen/fibronectin scaffold, facilitating fibroblast movement. HA production falls after about the fifth day of wound healing, and levels of chronroitin sulfate in dermatan sulfate increase. Fibronectin deposits in the collagen, and wound contraction begins. Biochemically during the contraction stage, hyaluronidase and proteinase are present, type I collagen synthesis is stimulated, and increased levels of chronroitin sulfate, dermatin sulfate and proteoglycans are observed; together these restructure the matrix. At the end of the healing process, the final scar shows collagen fibers mostly parallel to the epidermis.

Hypertrophic and keloid-type scars result in extension of scar tissue so that a bulky lesion results. A keloid is an exuberant scar that proliferates beyond the original wound. It should be noted that keloids only occur in humans, often causing burning, stinging and itching sensations as well as cosmetic embarrassment. The etiology of unsightly keloid formation is not known. However, in keloids, fibronectin formation continues for years, while fibronectin formation in normal scars disappears within a few days after wound closure. Keloid scars exhibit a high rate of collagen synthesis in comparison to normal scars, and a low proportion of cross-linked collagen.

Hypertrophic scars sometimes are difficult to distinguish from keloid scars histologically and biochemically, but unlike keloids, hypertropic scars remain confined to the injury site and often mature and flatten out over time. Both types secrete larger amounts of collagen than normal scars, but typically the hypertrophic type exhibits declining collagen synthesis after about six months. However, hypertrophic scars contain nearly twice as much glycosaminoglycan as normal scars, and this and enhanced synthetic and enzymatic activity result in significant alterations in the matrix which affects the mechanical properties of the scars, including decreased extensibility that makes them feel firm.

Atrophic scars are characterized by a thinning and diminished elasticity of the skin due to a loss of normal skin architecture. An example of an atrophic scar is striae distensae, also known as stretch marks. Striae commonly occur in postpartum women after childbirth and also during times of larger-than-average weight gain and also in association with steroids. Atrophic scars are sometimes also observed after trauma, infection and disease, and may show loss of surface markings and smoothness or dry, fine wrinkles over time.

Formation of scars, especially hypertrophic and keloid scars, is dependent on systemic growth factors such as interleukins and other cytokines, and their influence on fibronectin and collagen biosynthesis. Cytokines are released and are present in the wound healing process and, as mentioned above, are released in the inflammatory stage. Growth factors and other cytokines vary in the inflammatory stage and are released in amounts based, among other complex interactions, upon the redox state of the cells. The presence of free radicals in the inflammatory stage plays an important factor in wound healing. Factors that increase the presence of free radicals, such as infection, radiation, and continued trauma, may instigate hypertrophic and keloid scar formation. It is important to note that cytokines have been suggested to regulate nitric oxide synthetase, which controls the formation of nictric oxide, which plays an important role in signal transduction in the cells. It is also known that nitric oxide synthetase activity is aberrant in keloid scars when compared to normal tissue (Lim, T. C., et al., *Plastic and Reconst. Surgery*, 1996, 98: 911–912). Hypertrophic and keloid scars also show inflammatory activity that is not seen in mature scars.

Many scar treatments have been suggested, but few are satisfactory. Treatment of keloid or hypertrophic scars have consisted of surgical excision followed by injection of steroids and/or graft application. Pressure has also been used to cause scar thinning; for example, pressure bandages placed over scars have resulted in some scar thinning, but a pressure of at least about 25 mm Hg must be maintained constantly for approximately six months in usual situations for any visually observable effect. Ionizing radiation therapy has also been employed. Other treatments include application of silicone pads to the scar tissue surface, sometimes under pressure provided by an elastomeric bandage, topical application of silicone gel sheets, with or without added vitamin E (Palmieri, B., et al., *J. Derm.*, 1995, 34: 506–509), and topical or intralesional treatment with corticosteroids.

Scars are one of the strongest forces driving the cosmetic industry. It would be desirable to have alternative, preferably new and improved, treatments for scar reduction and remodeling. It would be desirable to have alternative topical compositions for skin wounds, particularly compositions that are efficient in free radical scavenging in membranes and inhibiting the inflammation and proinflammatory cascades, to make wounds heal more quickly and efficiently, with minimum scarring.

BRIEF SUMMARY OF THE INVENTION

It is an objective of the invention to provide new compositions and methods for the treatment of skin wounds and scar minimization. It is another and more specific objective of the invention to provide topical compositions for wound healing and simple methods for scar reduction and inhibition based upon direct topical application of compositions containing active ingredients and/or linaments such as a silicone gel sheet embedded with active ingredients, to scars and to injured skin sites susceptible to scarring.

These and other objectives of the invention are accomplished by the present invention, which provides therapies combining polyenylphosphatidyl choline (sometimes herein referred to as PPC) with at least one alkanolamine such as ethylaminoethanol, methylaminoethanol, dimethylaminoethanol, isopropanolamine, triethanolamine, isopropanoldimethylamine, ethylethanolamine, 2-butanolamine, choline, serine, and mixtures thereof, which are topically applied to skin wounds, to enhance repair and minimize scarring, often in association with a dermatologically acceptable carrier. The amount of PPC and alkanolamines necessary to treat wounded skin is not fixed per se, and necessarily is dependent upon the complement of dilinoleoyl and other unsaturated and polyunsaturated moities attached to the phosphatidylcholine molecular nucleus in the phosphatidylcholine portion of the preparation employed, the selection of the alkanolamine active component, the amount and type of any adjunct ingredients employed in the composition, the user's skin type, and the severity, extent, and nature of the wound treated. In some typical embodiments, the composition contains from about 0.25% to about 25%, more narrowly from about 0.25% to about 7% to 10% by weight, polyenylphosphatidylcholine, and from about 0.1 to about 10%, more narrowly from about 1% to about 3%, by weight alkanolamine such as dimethylaminoethanol. Higher concentrations of active ingredients may be used in bandage embodiments more fully discussed below. In one embodiment, from about 2% to about 3% by weight PPC is employed in combination with from about 1% to about 3% dimethylaminoethanol (hereinafter sometimes referred to as DMAE). Preferred compositions contain tyrosine as an adjunct ingredient.

DETAILED DESCRIPTION OF THE INVENTION

In the practice of the invention, a combination of polyenylphosphatidylcholine and an alkanolamine is used to treat skin wounds and promote healing when topically applied in effective amounts.

Any synthetic or natural polyenylphosphatidylcholine preparation may be employed in compositions of the invention. Natural preparations are preferred because they exhibit desirable physical characteristics and are both economical and nontoxic. By "polyenylphosphatidylcholine" is meant any phosphatidylcholine bearing two fatty acid substituents, wherein at least one is an unsaturated fatty acid with at least two double bonds. Preferred PPCs contain a mixture of substitutents such as those found in natural products. The fatty acids can be saturated or unsaturated and of any length, from $C_1$ (acetic) to $C_{28}$ (montanic), but typically range between $C_{12}$ and $C_{18}$ because most commercial products are vegetable oil extracts containing common fatty acids. Preferred polyenylphosphatidylcholines contain at least one linoleic (18:2) group, most preferably two, in a cis geometrical configuration typical of natural products, but some preparations contain linolenic (18:3) or eleostearic (20:3) groups in the doubly unsaturated component. As mentioned, preferred PPC compositions have dilinoleoylphosphatidylcholine (18:2—18:2 PC) as the most abundant PC species, present in the preparation at levels of at least about 25%, preferably at least about 40% by weight. A typical PPC preparation available from Rhône-Poulenc is a soybean extract containing about 42% dilinoleoylphosphatidylcholine and about 24% palmitoyllinoleylphosphatidylcholine (16:0–18:2 PC) as the major PC components.

Compositions of the invention contain an effective amount of an alkanolamine of the formula

wherein X, Y and Z are selected from the group consisting of hydrogen, $C_1$–$C_3$ alkyl groups, $C_2$–$C_4$ alkanol group, wherein at least one of X, Y, or Z is a $C_2$–$C_4$ alkanol group bearing at least one hydroxyl group and optionally at least one carboxyl group, are topically applied to wounds. Useful compounds for the invention include, but are not limited to, ethylaminoethanol, methylaminoethanol, dimethylaminoethanol, isopropanolamine, triethanolamine, isopropanoldimethylamine, ethylethanolamine, 2-butanolamine, choline, serine, and mixtures thereof. Many preferred embodiments employ methylaminoaminoethanol, dimethylaminoethanol, ethylaminoethanol, and/or triethanolamine; particularly preferred is dimethylaminoethanol (DMAE).

Effective amounts of PPC and alkanolamines are needed to treat skin wounds, and active ingredients may be applied sequentially or simultaneously using a composition that contains PPC and a second composition containing an alkanolamine, or a composition containing both ingredients. The latter is preferred for convenience of users. Since polyenylphosphatidylcholines are fat-soluble, PPC preparations can be applied neat to skin tissue. It is an advantage of the invention that one active compound is fatty so that it physically contributes to the lubrication of affected skin areas to which it is applied. In one embodiment, alkanolamines are simply dispersed in PPC, or lecithin formulations enriched with PPC, and applied to wounds.

In alternate embodiments, topical application to wounded skin sites is accomplished by applying the active ingredients in association with a carrier, and particularly one in which the PPC and alkanolamine active ingredients are soluble per se, or are effectively solubilized (e.g., as an emulsion or microemulsion). Where employed, the carrier is inert in the sense of not bringing about a deactivation or oxidation of the PPC and alkanolamine, and in the sense of not bringing about any adverse effect on the skin areas to which it is applied.

In one preferred practice of the invention, PPC and an alkanolamine are applied in admixture with a dermatologically acceptable carrier or vehicle (e.g., as a lotion, cream, ointment, soap, stick, or the like) so as to facilitate topical application and, in some cases, provide additional therapeutic effects as might be brought about, e.g., by moisturizing of the affected skin areas. While the PPC/alkanolamine carrier for dermatological compositions can consist of a relatively simple solvent or dispersant such as water, it is generally preferred that the carrier comprise a composition more conducive to topical application, and particularly one which will form a film or layer on the skin to which it is applied so as to localize the application and provide some resistance to washing off by immersion in water or by perspiration and/or aid in the percutaneous delivery of the active agent. Many preparations are known in the art, and include lotions containing oils and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. One preferred embodiment is an oil-in-water cream. Such compositions are referred to herein as dermally or dermatologically acceptable carriers.

Suitable carriers include water, alcohols, oils and the like, chosen for their ability to dissolve or disperse PPC, alkanolamine, and any other ingredients used in the treatment. Generally, even low concentrations of active ingredients in a carrier are suitable, depending upon the application regimen and adjunct ingredients employed. Many embodiments contain from about 0.1% to about 25% by weight, more narrowly from about 0.25% to about 5% to 10% by weight, PPC, and from about 0.1% to about 10% by weight, more narrowly from about 0.25% to about 5% to 7% by weight, and in many cases from about 1% to about 3% by weight, alkanolamine such as dimethylaminoethanol in the total composition. Minor wounds and scars typically require a lower concentration of active PPC/alkanolamine ingredients than do more serious ones. As a practical matter, however, to avoid the need for repeated application, it is desirable that the topically applied composition (i.e., PPC and alkanolamine plus carrier) be formulated to contain at least about 1% by weight PPC, and many embodiments contain more than 1 weight % PPC, and from about 2% to about 3% DMAE. One efficacious embodiment contains from about 2% to about 12% by weight PPC and from about 2% to about 3% DMAE, and this was employed in examples described below.

Generally in the practice of methods of the invention, the composition is topically applied to wounded skin areas in a predetermined or as-needed regimen either at intervals by application of a lotion or the like, it generally being the case that gradual improvement is noted with each successive application. Insofar as has been determined based upon clinical studies to date, no adverse side effects are encountered.

Alternative embodiments employ a silicone gel sheet or other linament to which polyenylphosphatidylcholine has been added. These may be pressure or adhesive bandages, gloves, or socks. Silicone gel sheets useful in the practice of the invention are typically cross-linked polydimethylsiloxane containing or impregnated with alkanolamine and PPC. It is an advantage of the invention that PPC and alkanolamines augment the effectiveness of previously disclosed methods of using lipoic acid and/or silicone pads or gel sheets for diminishing scars (see U.S. Pat. No. 5,965,618 to Perricone and Palmieri, et al., cited above). The concentration of active ingredients in bandage embodiments varies.

Some embodiments of this invention contain at least one other adjunct ingredient in addition to PPC and alkanolamines in wound treatments. Adjunct ingredients include, but are not limited to, tyrosine, and this is particularly preferred. Compositions of the invention that comprise tyrosine typically are formulated to contain from about 0.01% to about 6%, more narrowly from about 0.03% to about 5% by weight, and, in many embodiments, from about 0.2% to about 3% by weight tyrosine, based on the total composition. Compositions illustrated in the examples that follow contain from about 0.2% to about 1% tyrosine.

Wound- and scar-reducing topical compositions of the invention can comprise additional ingredients commonly found in skin care compositions, such as, for example, emollients, skin conditioning agents, emulsifying agents, humectants, preservatives, antioxidants, perfumes, chelating agents, etc., provided that they are physically and chemically compatible with other components of the composition. Preservatives include, but are not limited to, $C_1$–$C_3$ alkyl parabens and phenoxyenthanol, typically present in an amount ranging from about 0.5% to about 2.0% by weight percent, based on the total composition. Emollients, typically present in amounts ranging from about 0.01% to 5% of the total composition include, but are not limited to, fatty esters, fatty alcohols, mineral oils, polyether siloxane copolymers, and mixtures thereof. Humectants, typically present in amounts ranging from about 0.1% to about 5% by weight of the total composition include, but are not limited to, polyhydric alcohols such as glycerol, polyalkylene glycols (e.g., butylene glycol, propylene glycol, dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, and mixtures thereof. Emulsifiers, typically present in amounts from about 1% to about 10% by weight of the composition, include, but are not limited to, stearic acid, cetyl alcohol, stearyl alcohol, steareth 2, steareth 20, acrylates/$C_{10–30}$ alkyl acrylate crosspolymers, and mixtures thereof. Chelating agents, typically present in amounts ranging from about 0.01% to about 2% by weight, include, but are not limited to, ethylenediamine tetraacetic acid (EDTA) and derivatives and salts thereof, dihydroxyethyl glycine, tartaric acid, and mixtures thereof. Antioxidants, typically present in an amount ranging from about 0.02% to about 2.0% by weight of the composition, include, but are not limited to, butylated hydroxy toluene (BHT); vitamin C and/or vitamin C derivatives, such as fatty acid esters of ascorbic acid, particularly ascorbyl palmitate; lipoic acid; butylated hydroanisole (BHA); phenyl-α-naphthylamine; hydroquinone; propyl gallate; nordihydroquiaretic acid; vitamin E and/or derivatives of vitamin E, including tocotrienol and/or tocotrienol derivatives; calcium pantothenates; green tea extracts; mixed polyphenols; and mixtures of any of these. (See additional ingredients and methods in U.S. Pat. Nos. 4,775,530, 5,376,361, 5,409,693, 5,545,398, 5,574,063, 5,643,586, 5,709,868, 5,879,690, 5,965,618, 5,968,618, 6,051,244, 6,142,419, and 6,191,121 to Perricone).

Buffering agents are employed in many compositions. Preferably, the amount of buffering agent is one that results in compositions having a pH ranging from about 4.5 to about 8.5, more preferably from about 5.5 to about 8.5, most preferably from about 6.5 to about 8.0. Typical buffering agents are chemically and physically stable agents commonly found in cosmetics, and can include compounds that are also adjunct ingredients such as citric acid, malic acid, and glycolic acid buffers.

While not wishing to be bound to any theory, it is possible that PPC in combination with alkanolamines are efficacious in the treatment of skin damage because compositions containing them as active ingredients are fat-soluble and readily disperses in cell membranes and other cellular components. PPC readily penetrates skin. It also is an active antioxidant that has been shown to protect against lipid skin. It also is an active antioxidant that has been shown to protect against lipid peroxidation and liver damage, including fibrosis and cirrhosis (Aleynik, S. I., et al., *J. Investig. Med.* 47: 507–512 (1999)). Both PPC and alkanolamines act as free radical scavengers and neutralizers, and prevent the cross-linking of cell membranes that is often seen in its post-inflammatory phases. By the same token, PPC and alkanolamine modulation of free radicals and other oxidative species appear to affect gene expression, including expression of nuclear factor κ-B (NF-κB), nitric oxide synthetase and other mediators at all stages of proinflammation and inflammation. The alteration of lipid peroxidation, protein cross-linking, growth factor stimulation, and membrane permeability may explain the negative effect observed on the symptoms of skin damaged by wounds.

When skin is wounded and inflamed from irritants, trauma, surgery, dermabrasion, laser ablation, thermal burns, chemical burns, radiation burns (including sunburn) and other reasons, phospholipase-A-2 produces arachidonic acid from the phospholipid-rich membranes of the cell, resulting in the production of metabolites. We now know that stabilization of the cell membrane can inhibit the inflammatory cascade, therefore preventing the inflammatory response. It is also now known that arachidonic acid has a direct toxic effect on the mitochondria, resulting in the uncoupling of oxidative phosphorylation, resulting in free radical damage to the mitochondrial membrane. Polyenylphosphatidylcholine appears to intersperse in the cell membrane, stabilizing the membrane, and, at the same time, providing antioxidant capability. In addition, the incorporation of polyenylphosphatidylcholine into the cell membrane appears to enhance membrane activity, such as exchange of nutrients and wastes of the cellular environment. This also enhances cellular function and repair. Alkanolamines enhance these effects.

Methods and compositions of the present invention are particularly useful for treating cuts, minor abrasions and burns in skin tissue, surgical wounds, skin areas subjected to radiation therapy, post-laser and other dermatological procedures, the invention are useful in promoting wound healing and minimizing scar formation. Topical application of PPC and alkanolamines according to the invention can also be effective for the inhibition of microscarring of the dermis and to promote collagen production. It is an advantage of the invention that treatment or preventive measures employ, as an active ingredient, natural compounds. It is another advantage of the invention that topical application of PPC with alkanolamines provides a simple, non-invasive, nontoxic, over-the-counter topical method for treating all kinds of skin wounds. PPC and alkanolamines can also be employed over primary irritants such as Retin-A™ (tretinoin) application to counteract inflammation, and simultaneously enhance the effect of the other irritant (e.g., Retin-A™) used in acne treatments.

Compositions containing from about 3% to about 12% PPC by weight, from 2% to about 3% DMAE, and from about 0.2% to 1% tyrosine promoted healing of post-surgical incisions, small cuts, abrasions (including dermabrasion), laser ablation, and thermal, chemical, and radiation burns when applied topically, leading to wound resolution more rapid than that observed on untreated wounds, erythema was less visually apparent, and scar formation was less pronounced visually on skin areas treated with the inventive compositions. The compositions were also useful in the treatment of severe hand eczema and diaper area dermatitis.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the invention in any sequence which is effective to meet the objectives there intended, unless the context specifically indicates the contrary.

What is claimed is:

1. A method for the treatment of skin wounds comprising topically applying to the skin a composition containing an effective amount of polyenylphosphatidylcholine and an effective amount of an alkanolamine of the formula

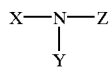

wherein X, Y and Z are selected from the group consisting of hydrogen, $C_1$–$C_3$ alkyl groups, $C_2$–$C_4$ alkanol group, wherein at least one of X, Y, or Z is a $C_2$–$C_4$ alkanol group bearing at least one hydroxyl group and optionally at least one carboxyl group.

2. A method according to claim 1 wherein dilinoleoylphosphatidylcholine is the most abundant phosphatidylcholine species in the polyenylphosphatidylcholine component of the composition, and the alkanolamine is selected from the group consisting of ethylaminoethanol, methylaminoethanol, dimethylaminoethanol, isopropanolamine, triethanolamine, isopropanoldimethylamine, ethylethanolamine, 2-butanolamine, choline, serine, and mixtures thereof.

3. A method according to claim 2 wherein dilinoleoylphosphatidylcholine comprises at least about 25% by weight of the polyenylphosphatidylcholine component.

4. A method according to claim 1 wherein the composition comprises from about 0.25% to about 12% by weight polyenylphosphatidylcholine, and from about 0.1% to about 10% by weight alkanolamine.

5. A method according to claim 4 wherein the composition contains from about 1% to about 12% by weight polyenylphosphatidylcholine, and from about 1% to about 3% alkanolamine.

6. A method according to claim 4 wherein the composition also contains from about 0.1% to about 5% by weight tyrosine.

7. A method according to claim 3 wherein the composition contains at least about 40% by weight dilinoleoylphosphatidyl choline in the polyenylphosphatidylcholine, and the alkanolamine is dimethylaminoethanol.

8. A method according to claim 6 wherein the polyenylphosphatidylcholine is obtained from soybean oil.

9. A method according to claim 1 wherein the skin wound is a cut or an abrasion.

10. A method according to claim 1 wherein the skin wound is a burn.

11. A method according to claim 1 wherein the skin wound is a blemish.

12. A method according to claim 1 which inhibits the formation of cutaneous scar tissue.

13. A method according to claim 1 wherein the composition is applied as a bandage.

14. A bandage impregnated with a composition containing an effective wound-healing amount of polyenylphosphatidylcholine and an alkanolamine selected from the group consisting of ethylaminoethanol, methylaminoethanol, dimethylaminoethanol, isopropanolamine, triethanolamine, isopropanoldimethylamine, ethylethanolamine, 2-butanolamine, choline, serine, and mixtures thereof.

15. A bandage according to claim 14 wherein dilinoleoylphosphatidylcholine comprises at least about 25% by weight of the polyenylphosphatidylcholine component, and the alkanolamine is dimethylaminoethanol.

16. A bandage according to claim 14 wherein the composition comprises from about 0.25% to about 10% by weight polyenylphosphatidylcholine, and from about 0.1% to about 10% alkanolamine.

17. A bandage according to claim 16 wherein the composition contains from about 1% to about 8% by weight polyenylphosphatidylcholine, and from about 1% to about 3% by weight alkanolamine.

18. A bandage according to claim 15 wherein the composition contains at least about 40% by weight dilinoleoylphosphatidyl choline in the polyenylphosphatidylcholine, and the alkanolamine is dimethylaminoethanol.

19. A bandage according to claim 18 wherein the polyenylphosphatidylcholine is obtained from soybean oil.

20. A bandage according to claim 14 which is a silicone gel sheet.

21. A bandage according to claim 14 wherein the composition further contains tyrosine.

22. A method for the treatment of skin wounds comprising topically applying to the skin a composition containing an effective wound-healing amount of polyenylphosphatidylcholine and another composition containing an alkanolamine selected from the group consisting of ethylaminoethanol, methylaminoethanol, dimethylaminoethanol, isopropanolamine, triethanolamine, isopropanoldimethylamine, ethylethanolamine, 2-butanolamine, choline, serine, and mixtures thereof.

23. A method according to claim 22 wherein either or both compositions further contain tyrosine.

24. A method according to claim 23 wherein the polyenylphosphatidyl choline composition comprises from about 0.25% to about 12% by weight polyenylphosphatidylcholine and the alkanolamine composition comprises from about 0.1% to about 10% by weight alkanolamine.

25. A composition for treating skin wounds comprising polyenylphosphatidylcholine and an alkanolamine of the formula

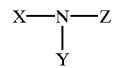

wherein X, Y and Z are selected from the group consisting of hydrogen, $C_1$–$C_3$ alkyl groups, $C_2$–$C_4$ alkanol group, wherein at least one of X, Y, or Z is a $C_2$–$C_4$ alkanol group bearing at least one hydroxyl group and optionally at least one carboxyl group.

26. A composition according to claim 25 wherein dilinoleoylphosphatidylcholine is the most abundant phosphatidylcholine species in the polyenylphosphatidylcholine component of the composition, and the alkanolamine is selected from the group consisting of ethylaminoethanol, methylaminoethanol, dimethylaminoethanol, isopropanolamine, triethanolamine, isopropanol dimethylamine, ethylethanolamine, 2-butanolamine, choline, serine, and mixtures thereof.

27. A composition according to claim 26 wherein dilinoleoylphosphatidylcholine comprises at least about 25% by weight of the polyenylphosphatidylcholine component.

28. A composition according to claim 26 wherein the composition comprises from about 0.25% to about 25% by weight polyenylphosphatidylcholine, and from about 0.1% to about 10% by weight alkanolamine.

29. A composition according to claim 28 wherein the composition contains from about 1% to about 12% by weight polyenylphosphatidylcholine, and from about 1% to about 3% alkanolamine.

30. A composition according to claim 28 wherein the composition also contains from about 0.1% to about 5% by weight tyrosine.

* * * * *